United States Patent [19]

Singerman et al.

[11] 4,400,282
[45] Aug. 23, 1983

[54] LUBRICATING OILS CONTAINING QUATERNARY AMMONIUM THIOMOLYBDATES

[75] Inventors: Gary M. Singerman, Monroeville; Yumi P. Ryu, Murrysville; James R. Anglin, Gibsonia, all of Pa.

[73] Assignee: Gulf Research & Development Company, Pittsburgh, Pa.

[21] Appl. No.: 216,140

[22] Filed: Dec. 15, 1980

Related U.S. Application Data

[63] Continuation-in-part of Ser. No. 213,676, Dec. 5, 1980, Pat. No. 4,343,747, and Ser. No. 214,972, Dec. 10, 1980, Pat. No. 4,343,746.

[51] Int. Cl.³ .............................................. C10M 1/48
[52] U.S. Cl. ............................. 252/32.7 E; 252/34.7; 252/49.7

[58] Field of Search ................ 252/46.7, 32.7 E, 46.4, 252/49.7, 34, 34.7

[56] References Cited

U.S. PATENT DOCUMENTS

| | | | |
|---|---|---|---|
| 2,909,541 | 10/1959 | Hugel | 252/47.5 X |
| 3,223,625 | 12/1965 | Cyphers et al. | 252/46.4 X |
| 3,272,746 | 9/1966 | Le Suer et al. | 252/47.5 |
| 3,290,245 | 12/1966 | Elliott et al. | 252/46.4 X |
| 3,390,082 | 6/1968 | Le Suer et al. | 252/32.7 E |
| 3,997,454 | 12/1976 | Adams | 252/46.7 X |

Primary Examiner—Andrew Metz
Attorney, Agent, or Firm—Deane E. Keith; Forrest D. Stine; Donald L. Rose

[57] ABSTRACT

Hydrocarbon lubricating oils with a tetrahydrocarbylammonium thiomolybdate having at least about 19 carbon atoms, such as dicocodimethylammonium thiomolybdate, solubilized in the oil are characterized by improved anti-friction properties.

12 Claims, No Drawings

LUBRICATING OILS CONTAINING QUATERNARY AMMONIUM THIOMOLYBDATES

This application is a continuation-in-part of U.S. Ser. No. 213,676, filed Dec. 5, 1980, now U.S. Pat. No. 4,343,747, and U.S. Ser. No. 214,972, filed Dec. 10, 1980, now U.S. Pat. No. 4,343,746.

SUMMARY OF THE INVENTION

This invention relates to hydrocarbon lubricating oils having improved antifriction properties comprising a minor amount of a quaternary ammonium thiomolybdate, more specifically defined as a tetrahydrocarbyl ammonium thiomolybdate, dissolved in the oil.

DESCRIPTION OF THE INVENTION

The lubricating properties of molybdenum disulfide in petroleum based lubricating oils are well known. Since molybdenum disulfide is insoluble in the lubricating oil, it is provided as a dispersion in the oil with the particle size being less than one micrometer in good quality commercial dispersions. This gives the oil a black appearance which can visually be confused with badly contaminated spent motor oil. In view of this insolubility of the molybdenum disulfide in the oil together with a specific gravity almost five times that of the oil, its use in motor oils is restricted. Practicable oil-soluble, friction-reducing compounds containing molybdenum and sulfur have been sought for commercial utilization.

In accordance with our invention, we have discovered a class of molybdenum sulfides which can be solubilized in hydrocarbon lubricating oils and which enhance the lubricating properties of these oils as evidenced by a substantial reduction in the coefficient of friction of the oils. As part of our invention, we have discovered a method for solubilizing these molybdenum sulfides in the hydrocarbon lubricating oils. These molybdenum sulfides are certain members of the larger class of tetrahydrocarbyl ammonium thiomolybdates, many of which cannot be solubilized in hydrocarbon oils by our invention. Those tetrahydrocarbyl ammonium thiomolybdates which can be solubilized in hydrocarbon oils and which are useful oil additives in accordance with our invention are defined by the general formula

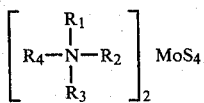
(1)

wherein $R_1$ and $R_2$ are selected from straight or branched chain alkyl or alkenyl having from about one to about 30 carbon atoms, preferably about one to about 20 carbon atoms; $R_3$ is independently selected from straight or branched chain alkyl or alkenyl having from about one to about 30 carbon atoms, preferably from about 12 to about 20 carbon atoms; and $R_4$ is straight or branched chain alkyl or alkenyl having from about 12 to about 30 carbon atoms, preferably about 12 to about 20 carbon atoms; and where the total number of carbon atoms in $R_1$, $R_2$, $R_3$ and $R_4$ is at least about 19 carbon atoms, preferably at least about 25 carbon atoms with a maximum of about 80 carbon atoms, preferably a maximum of about 60 carbon atoms.

Mixtures of tetrahydrocarbyl ammonium thiomolybdates having different alkyl and/or alkenyl groups as defined above are also included herein whether prepared by mixing together two or more different tetrahydrocarbyl ammonium thiomolybdates or prepared from a mixture of precursor compounds, such as the reaction of a mixture of tetrahydrocarbyl ammonium salts with a thiomolybdate salt. The alkyl and alkenyl groups can be derived using conventional procedures from the naturally occurring mixture of fatty acids in animal or vegetable fats and oils. As used herein, the term alkenyl includes mono-, di- and tri-olefinic groups.

Some quaternary ammonium thiomolybdates which are useful in accordance with our invention are
dicocodimethylammonium thiomolybdate,
ditallowdimethylammonium thiomolybdate,
dialkyl($C_{12}$–$C_{18}$)dimethylammonium thiomolybdate,
distearyldimethylammonium thiomolybdate,
bis(hydrogenated-tallow)dimethylammonium thiomolybdate,
hexadecyltrimethylammonium thiomolybdate,
octadecyltrimethylammonium thiomolybdate,
soyatrimethylammonium thiomolybdate,
tris(hydrogenated-tallow)methylammonium thiomolybdate,
tricocomethylammonium thiomolybdate, and mixtures thereof.

However, many additional useful compounds as defined by the above formula are not specifically set out herein.

In general these tetrahydrocarbyl ammonium thiomolybdates are not by themselves soluble in hydrocarbon lubricating oils such as petroleum oils, hydrogenated polyalpha-olefin oligomers, and the like. However, we have discovered in accordance with our invention that these hydrocarbon oil-insoluble tetrahydrocarbyl ammonium thiomolybdates as defined by the above formula can be solubilized in hydrocarbon oils. We have discovered that the combination of a suitable zinc dialkyl dithiophosphate and a suitable dispersant can be used to effect the solubilizing of the thiomolybdate in the hydrocarbon oil.

The preferred class of zinc dialkyl dithiophosphates is defined by the formula

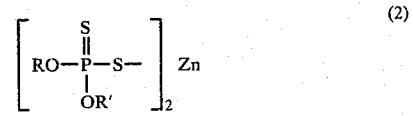
(2)

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl, n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid diester will average about 5 or greater.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5.

The preferred dispersants are ashless dispersants and a preferred class of ashless dispersants are the nitrogen-containing dispersant additives which are generally known in the art as sludge dispersants for crankcase motor oils. These dispersants include mineral oil-soluble slats, alkyl phenols, high molecular weight alcohols, amides, imides and esters made from high molecular weight mono- and dicarboxylic acids (and where they exist the corresponding acid anhydrides) and various amines or nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1.

Primarily because of its ready availability and low cost, the hydrocarbon portion of the mono- or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal containing dispersant. These polyalkyleneamines include those represented by the general formula

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di(2-aminoethyl)ethylenediamine may also be used. Other aliphatic polyamino compounds that may be used are N-aminoalkyl-piperazines, e.g., N-(2-aminoethyl)-piperazine. Mixtures of alkylene polyamines approximating tetraethylene pentamine are commercially available, e.g., Dow E-100 sold by Dow Chemical Company of Midland, Michigan.

Representative dispersants are formed by reacting about one molar amount of polyisobutenyl succinic anhydride with from about one to about two molar amounts of tetraethylene pentamine or with from about 0.5 to 1 moles of a polyol, e.g., pentaerythritol.

In general the ashless dispersant can be used in the lubricating oil broadly in a range of from about 0.1 to about 15 weight percent and preferably is used in the range of between about one to about ten percent. However, care should be exercised that a sufficient quantity of the zinc dialkyl dithiophosphate and the dispersant are used to effect the dissolving of the particular thiomolybdate into the hydrocarbon oil. For example, more of these solubilizers are required for dissolving hexadecyltrimethylammonium thiomolybdate than is required for an equal weight of tris(hydrogenated-tallow)methylammonium thiomolybdate.

The quaternary ammonium thiomolybdates which are useful herein are semi-solid to solid compounds with a brick red to dark red color. They decompose at a temperature between about 170° to about 200° C., depending on the specific compound, turning black upon decomposition. The mechanism of their activity in improving the lubricating properties of mineral oils is not understood. The coefficient of friction substantially decreases when a mineral oil solution containing one percent of a thiomolybdate such as dicocodimethylammonium thiomolybdate is elevated in temperature from 54° C. to 121° C. This suggests that a chemical reaction is involved but it does not appear that such reaction is the decomposition of the thiomolybdate to molybdenum disulfide since one percent of the thiomolybdate is equivalent to 0.15 percent molybdenum disulfide which is below the level of effectiveness of molybdenum disulfide.

The lubricating oils of the present invention, in which the lubricating properties have been improved by the presence in solution of the tetrahydrocarbyl ammonium thiomolybdate, are particularly suitable for use as motor oils in internal combustion engines such as used in automobiles, trucks, motor-generator sets and the like. The expressions hydrocarbon oils and hydrocarbon lubricating oil, as used herein, refer to base oils which consist primarily of hydrocarbon molecules, but the expressions contemplate the presence in mineral oils of relatively small amounts of naturally occurring sulfur, sulfur-containing hydrocarbons, and the like. However, the expressions do not include the presence of significant quantities of oxygen-containing organic compounds such as the fatty glycerides, acids or esters, and the like. Although the quaternary ammonium compounds are more readily soluble in these fatty compounds, the presence of oxygen-containing compounds such as these fatty compounds is undesirable in motor oils because they lead to undesired decomposition products at the elevated temperatures present in internal combustion engines. The hydrocarbon oils can be obtained from naturally occurring sources such as petroleum, tar sands, shale oil, and the like, or they can be synthetic hydrocarbon oils, such as those obtained by polymerization of olefins, particularly 1-olefins, to the lubricating range such as the trimer and tetramer of 1-decene, and the like.

The tetrahydrocarbyl ammonium thiomolybdate can be used in the hydrocarbon lubricating oil in an amount between about 0.1 to about six weight percent, but superior results are generally obtained in the preferred range of between about 0.5 to about three weight percent.

The tetrahydrocarbyl ammonium thiomolybdates can be prepared by the reaction of the corresponding quaternary ammonium salt such as the halide or sulfate with an alkali metal thiomolybdate. Since the alkali metal thiomolybdate is soluble in water and since most of the quaternary ammonium salts corresponding to the tetrahydrocarbyl ammonium thiomolybdate of formula (1) are not soluble in water, we have found that these water-insoluble quaternary ammonium salts can be dissolved in an organic solvent such as toluene or methylene chloride and reacted by agitating this solution and the aqueous alkali metal thiomolybdate in a two-phase reaction. The resulting tetrahydrocarbyl ammonium thiomolybdate product is dissolved in the organic solvent from which it is separated. When the quaternary ammonium salt is soluble in water, which is the case with salts having a relatively low number of carbon atoms in the molecule, such as hexadecyltrimethylammonium chloride, the reaction can be carried out in a single-phase, aqueous reaction. However, the thiomolybdates prepared from these water-soluble salts have a somewhat restricted utility because of their reduced solubility in the hydrocarbon oils. The alkali metal thiomolybdate can be prepared by reacting an alkaline aqueous solution of an alkali metal molybdate with hydrogen sulfide gas.

The naturally occurring fatty acids are an excellent and convenient source for the higher molecular weight alkyl and alkenyl groups in the quaternary ammonium thiomolybdate. These fatty acids can be converted to the corresponding alkenyl group and saturated, if desired, by conventional hydrogenation procedures. For example, oleic acid can be converted to octadecenyl and this can be hydrogenated to octadecyl. Since the naturally occurring fats comprise mixtures of two and generally more carbon chains of different lengths, the resulting quaternary compounds containing the alkenyl and alkyl groups in the same relative proportion as the precursor acids occur in the fat. The relative proportion of alkyl and alkenyl groups of various chain lengths that are derived from different natural sources referred to herein is set out in the following table in which coco is derived from coconut oil, tallow and stearyl are derived from beef fat and soya is derived from soya bean oil.

TABLE I

| chain length | coco | tallow | stearyl | soya |
|---|---|---|---|---|
| $C_8$ | 5 | — | — | — |
| $C_{10}$ | 8 | — | — | — |
| $C_{12}$ | 50 | — | — | — |
| $C_{14}$ | 18 | 5 | — | — |
| $C_{16}$ | 8 | 30 | 8 | 15 |
| $C_{17}$ | — | — | 1 | — |
| $C_{18}$ | 11 | 65 | 91 | 85 |

DESCRIPTION OF PREFERRED EMBODIMENTS

EXAMPLE 1

The preparation of a tetrahydrocarbyl ammonium thiomolybdate from a water-insoluble tetrahydrocarbyl ammonium salt in a two-phase reaction is described. A 360 g quantity of a commercial mixture containing 75 percent dicocodimethylammonium chloride (0.615 mol) and 25 percent isopropanol was dissolved in one liter of toluene and this solution was stirred with an aqueous solution containing 102 g (0.337 mol) of potassium thiomolybdate in one liter of water at room temperature for 30 minutes. After separating out the dark red toluene layer and water washing it, the toluene was removed under reduced pressure. A quantitative yield of semi-solid, dark red dicocodimethylammonium thiomolybdate was obtained. Analysis of the product for thiomolybdate ion by infrared spectroscopy showed a band at 460 cm$^{-1}$ and by ultraviolet-visible spectroscopy in toluene showed a band at 470 nm. The calculated elemental analysis for dicocodimethylammonium thiomolybdate was N, 2.7%, S, 12.2% and Mo, 9.15%. The actual elemental analysis was N, 2.63%, S, 12.44% and Mo, 9.3%.

EXAMPLE 2

The preparation of a mixture of tetrahydrocarbyl ammonium thiomolybdates is described. A solution containing 3.9 g (9 mmol) of a 1:1 molar mixture of tallowtrimethylammonium chloride and dicocodimethylammonium chloride and 50 percent isopropanol was dissolved in 100 ml of toluene. This solution was vigorously stirred with a solution containing 1.5 g of potassium thiomolybdate in 50 ml of water for about 15 minutes. The organic layer was separated from the aqueous layer and the organic solvent removed at reduced pressure. A dark red semi-solid mixture (7 g) of tallowtrimethylammonium thiomolybdate and dicocodimethylammonium thiomolybdate was recovered.

EXAMPLE 3

The effects of a succinimide-type ashless dispersant (Lubrizol 941) and a zinc dialkyl dithiophosphate (Lubrizol 1395) on the solubility of dicocodimethylammonium thiomolybdate in a mineral base oil comprising 54 volume percent of a light neutral oil and 46 percent of a medium neutral oil were studied. The results are set out in Table II. In preparing the solutions, the additives were mixed together, then the base oil was added and stirred at 60° C. After standing overnight, the solubility was rated at about 20° C.

TABLE II

| Blend Number | 1 | 2 | 3 | 4 |
|---|---|---|---|---|
| Makeup, volume % | | | | |
| base oil | 99 | 94 | 98 | 93 |
| dispersant | — | 5 | — | 5 |
| dithiophosphate | — | — | 1 | 1 |
| thiomolybdate | 1 | 1 | 1 | 1 |
| Solubility | none | slight | partial | complete |

In this experiment no solubility was evidenced by no color change in the oil and all of the solid thiomolybdate remained on the bottom. Slight solubility was evidenced by a color change in the solution with most of the thiomolybdate remaining on the bottom. Partial solubility was evidenced by part of the thiomolybdate being on the bottom, part being in suspension and part being in solution. Complete solubility was evidenced by a clear solution with no solid thiomolybdate being visible.

The following experiments were carried out using a commercial grade automotive motor oil which contained 46.6 volume percent of a light neutral oil, 40 percent of a medium netural oil, 6.1 percent of a commercial additive package which provided about one percent of a zinc dialkyl dithiophosphate and about 4 to 5 percent of a succinimidetype dispersant to the oil, and about 7.3 percent of a viscosity index improver. The oil analyzed 0.156 weight percent zinc. The 40° C. viscosity of the oil was 77.1 mm$^2$/s (cSt) and the 100° C. viscosity was 13.34 mm$^2$/s (cSt).

The coefficient of friction was determined by the ASTM D2266-67 Four-Ball Method as set out in the following description. The Precision Scientific Company of Chicago, Ill., four-ball wear tester was used. This tester was modified for these tests by utilizing a strain gage load cell, a strain gage bridge amplifier, and a strip chart recorder to measure and record the frictional force between the upper rotating ball and the three lower stationary balls. In testing, the friction force generally reached steady state conditions after one minute. The average coefficient of friction was determined by averaging the one-minute reading and seven additional equally spaced readings. The test was carried out at 54° C. (130° F.) and 121° C. (250° F.) at 1,200 rpm and a load of 20 kg for three hours.

EXAMPLE 4

A series of quaternary ammonium thiomolybdates (QATM) were tested in the test motor oil. In all cases one weight percent of the thiomolybdate was used. The following Table III sets out the various coefficients of friction as determined by this series of tests.

TABLE III

| | Coefficient of Friction | | | |
|---|---|---|---|---|
| | at 54° C. (130° F.) | | at 121° C. (250° F.) | |
| | at 3 hrs. | Ave. | at 3 hrs. | Ave. |
| Motor oil, no QATM | 0.156 | 0.147 | 0.145 | 0.146 |
| QATM added, 1 wt. % | | | | |
| dicocodimethyl | 0.119 | 0.124 | 0.026 | 0.019 |
| tallow-dicoco[a] | — | — | 0.068 | 0.073 |
| soya-dicoco[b] | — | — | 0.085 | 0.097 |
| dioctadecyldimethyl | — | — | 0.043 | 0.026 |
| hexadecyltrimethyl[c] | 0.111 | 0.109 | 0.017 | 0.031 |
| dialkyldimethyl[d] | 0.094 | 0.094 | 0.009 | 0.049 |
| ditallowdimethyl[e] | 0.085 | 0.090 | 0.094 | 0.094 |
| tritallowmethyl[e] | 0.111 | 0.112 | 0.008 | 0.085 |
| benzylalkyldimethyl[d] | 0.119 | 0.105 | 0.119 | 0.131 |

[a] 1:1 molar mixture of tallowtrimethyl- and dicocodimethylammonium thiomolybdate
[b] 1:1 molar mixture of soyatrimethyl- and dicocdimethylammonium thiomolybdate
[c] not completely soluble in the oil
[d] alkyl is a mixture of 12, 14 and 16 carbon atom alkyl groups
[e] tallow is hydrogenated The data in the above table demonstrates that the reduction in the coefficient of friction of the base oil when the tetrahydrocarbylammonium thiomolybdate contains four alkyl or alkenyl groups and fits formula (1) above is substantial. However, when the thiomolybdate contains an aromatic group, such as in the case of benzylalkyldimethylammonium thiomolybdate, the reduction in the coefficient of friction at 121° C. is not impressive.

EXAMPLE 5

A series of experiments was carried out to determine the effect on the coefficient of friction of the test motor oil using different quantities of dicocodimethylammonium thiomolybdate at 54° C. and 121° C. The results of these experiments are set out in Table IV.

TABLE IV

| | Coefficient of Friction | | | |
|---|---|---|---|---|
| | at 54° C. (130° F.) | | at 121° C. (250° F.) | |
| Thiomolybdate, wt. % | at 3 hrs. | Ave. | at 3 hrs. | Ave. |
| 0 | 0.156 | 0.147 | 0.145 | 0.146 |
| 0.1 | 0.136 | 0.138 | 0.136 | 0.138 |
| 0.5 | 0.102 | 0.104 | 0.077 | 0.085 |
| 1.0 | 0.119 | 0.124 | 0.026 | 0.019 |
| 2.0 | 0.077 | 0.078 | 0.060 | 0.063 |
| 3.0 | 0.094 | 0.099 | 0.098 | 0.086 |
| 6.0 | — | — | 0.128 | 0.100 |

EXAMPLE 6

A further series of experiments was carried out to determine the effect on the coefficient of friction of the test oil using one weight percent dicocodimethylammonium thiomolybdate at different temperatures. The results of these runs are set out in Table V.

TABLE V

| | Temperature | | | |
|---|---|---|---|---|
| Coefficient of friction | 54° C. (130° F.) | 100° C. (212° F.) | 121° C. (250° F.) | 150° C. (302° F.) |
| at 1 minute | 0.145 | 0.128 | 0.043 | 0.094 |
| at 3 hours | 0.119 | 0.068 | 0.026 | 0.084 |
| average | 0.124 | 0.077 | 0.019 | 0.044 |

EXAMPLE 7

The effect on the coefficient of friction of molybdenum disulfide crystals in the test oil was compared with dicocodimethylammonium thiomolybdate (DCDM). The molybdenum disulfide crystals were added as a 15 weight percent suspension of the molybdenum disulfide in a carrier oil. The results are set out in Table VI, which records the total amount of molybdenum disulfide additive that was used.

TABLE VI

| | Coefficient of Friction | | | |
|---|---|---|---|---|
| | at 54° C. (130° F.) | | at 121° C. (250° F.) | |
| | at 3 hrs. | Ave. | at 3 hrs. | Ave. |
| Motor oil | 0.156 | 0.147 | 0.145 | 0.146 |
| Additive, wt. % | | | | |
| 1% DCDM | 0.119 | 0.124 | 0.026 | 0.019 |
| 1% MoS₂ Susp. | 0.136 | 0.134 | 0.162 | 0.155 |

Since one percent dicocodimethylammonium thiomolybdate is equivalent to about 0.15 percent molybdenum disulfide and since 0.15 percent molybdenum disulfide itself is present in the molybdenum disulfide suspension, these two experiments are directly comparable.

It is to be understood that the above disclosure is by way of specific example and that numerous modifications and variations are available to those of ordinary skill in the art without departing from the true spirit and scope of the invention.

We claim:

1. A lubricating oil composition comprising a major portion of a hydrocarbon lubricating oil comprising in solution (a) at least a friction reducing amount of a tetrahydrocarbylammonium thiomolybdate having the formula

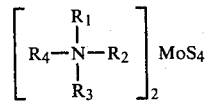

wherein $R_1$, $R_2$ and $R_3$ are independently selected from straight and branched alkyl and alkenyl having from one to about 30 carbon atoms, $R_4$ is straight or branched alkyl or alkenyl having from about 12 to about 30 carbon atoms and the total number of carbon atoms in $R_1$, $R_2$, $R_3$ and $R_4$ is between about 19 and about 80 carbon atoms, and (b) a sufficient amount of (1) a zinc dialkyl dithiophosphate and (2) an ashless dispersant to solubilize said tetrahydrocarbylammonium thiomolybdate in the hydrocarbon lubricating oil.

2. A lubricating oil composition in accordance with claim 1 wherein $R_1$ and $R_2$ independently have from about 1 to about 20 carbon atoms, $R_3$ and $R_4$ independently have from about 12 to about 20 carbon atoms, and the total number of carbon atoms in $R_1$, $R_2$, $R_3$ and $R_4$ is between about 25 and about 60 carbon atoms.

3. A lubricating oil composition in accordance with claim 2 wherein $R_1$ and $R_2$ are methyl.

4. A lubricating oil composition in accordance with claim 2 wherein $R_1$ is methyl and $R_2$ has between about 12 and about 20 carbon atoms.

5. A lubricating oil composition in accordance with claim 2 wherein said thiomolybdate is dicocodimethylammonium thiomolybdate.

6. A lubricating oil composition in accordance with claim 2 wherein said thiomolybdate is bis(hydrogenatedtallow)dimethylammonium thiomolybdate.

7. A lubricating oil composition in accordance with claim 3 wherein said thiomolybdate is tris(hydrogenatedtallow)methylammonium thiomolybdate.

8. A lubricating oil composition in accordance with claim 1 comprising from about 0.1 to about six weight percent of said tetrahydrocarbylammonium thiomolybdate.

9. A lubricating oil composition in accordance with claim 1 comprising from about 0.5 to about three weight percent of said tetrahydrocarbylammonium thiomolybdate.

10. A lubricating oil composition in accordance with claim 1 wherein said zinc dialkyl dithiophosphate has the formula

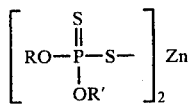

wherein R and R' are independently selected from hydrocarbyl radicals having from 1 to about 18 carbon atoms.

11. A lubricating oil composition in accordance with claim 10 wherein R and R' are independently selected from alkyl radicals having from about 2 to about 12 carbon atoms.

12. A lubricating oil composition in accordance with claim 1 comprising from about 0.01 to about 5 weight percent of said zinc dialkyl dithiophosphate and from about 0.1 to about 15 weight percent of said ashless dispersant.

* * * * *